(12) United States Patent
Cameron (10) Patent No.: US 7,450,992 B1
(45) Date of Patent: Nov. 11, 2008

(54) METHOD FOR CONTROLLING OR REGULATING THERAPEUTIC NERVE STIMULATION USING ELECTRICAL FEEDBACK

(75) Inventor: Tracy L. Cameron, Toronto (CA)

(73) Assignee: Advanced Neuromodulation Systems, Inc., Plano, TX (US)

( * ) Notice: Subject to any disclaimer, the term of this patent is extended or adjusted under 35 U.S.C. 154(b) by 322 days.

(21) Appl. No.: 11/206,497

(22) Filed: Aug. 18, 2005

(51) Int. Cl.
*A61N 1/34* (2006.01)

(52) U.S. Cl. .......................................... 607/46; 607/62

(58) Field of Classification Search ...................... 607/2, 607/45, 46, 59, 62
See application file for complete search history.

(56) References Cited

U.S. PATENT DOCUMENTS

| | | | | |
|---|---|---|---|---|
| 5,702,429 A | * | 12/1997 | King | 607/46 |
| 5,792,212 A | | 8/1998 | Weijand | 607/73 |
| 5,902,236 A | | 5/1999 | Iversen | 600/377 |
| 6,011,996 A | | 1/2000 | Gielen et al. | 607/116 |
| 6,091,979 A | | 7/2000 | Madsen | 600/377 |
| 6,301,492 B1 | | 10/2001 | Zonenshayn | 600/378 |
| 6,606,521 B2 | | 8/2003 | Paspa et al. | 607/116 |
| 6,609,031 B1 | | 8/2003 | Law et al. | |
| 2005/0246004 A1 | * | 11/2005 | Cameron et al. | 607/116 |

* cited by examiner

*Primary Examiner*—Kennedy J Schaetzle
(74) *Attorney, Agent, or Firm*—Christopher S. L. Crawford; Peter Lando; Melissa Acosta (57) ABSTRACT

A stimulation system includes a stimulation source, an implantable stimulation lead, an implantable sensing device, and a controller. The stimulation source generates and transmits stimulation pulses to stimulation electrodes on the stimulation lead. The stimulation electrodes deliver the stimulation pulses to target nerve tissue in a nerve pathway to cause paresthesia in a portion of the person's body. Each stimulation pulse induces an action potential in a number of nerve fibers in the nerve pathway. The sensing device includes sensing electrodes positioned proximate the nerve pathway that detect compound action potentials of nerve fibers stimulated by the stimulation pulses. The controller modifies the stimulation pulses generated by the stimulation source and delivered to the target nerve tissue by the stimulation electrodes based on the detected compound action potentials to maintain a substantially constant level of paresthesia in the portion of the person's body.

11 Claims, 7 Drawing Sheets

METHOD FOR CONTROLLING OR REGULATING THERAPEUTIC NERVE STIMULATION USING ELECTRICAL FEEDBACK

TECHNICAL FIELD

This invention relates generally to electrical stimulation for medical purposes and in particular to systems and methods for controlling or regulating therapeutic nerve stimulation using electrical feedback.

BACKGROUND

Electrical energy may be applied to the spinal cord or a peripheral nerve, for example, to treat regions of the body that are affected by chronic pain from a variety of etiologies. The electrical energy is delivered through electrodes positioned proximate the nerve tissue to be stimulated, for example, external to the dura surrounding the spinal cord. The electrical energy stimulates target nerve tissue to cause a subjective sensation of numbness or tingling in the affected region of the body, known as "paresthesia." The electrodes may be carried by either of two primary vehicles: a percutaneous lead and a laminotomy or "paddle" lead.

Percutaneous leads typically have three or more equally-spaced electrodes. They are positioned using a needle that is passed through the skin and, for example, between the desired vertebrae and onto the top of the dura. Percutaneous leads deliver energy radially in all directions because of the circumferential nature of the electrode. Paddle leads have a paddle-like configuration and typically have multiple electrodes arranged in one or more columns. Paddle leads provide more focused energy delivery than percutaneous leads because electrodes may be present on only one surface of the lead. Paddle leads may be desirable in certain situations because they provide more direct stimulation to the target nerve tissue and require less energy to produce a desired effect.

When electrical energy is applied to nerve tissue using such stimulation electrodes at an intensity above the threshold of the nerve tissue, an action potential is generated within individual nerve fibers that are stimulated. The number of nerve fibers that are stimulated is directly related to the intensity of the stimulation. The intensity of the stimulation is directly related to the distance between the stimulation electrodes and the nerve tissue and affects the level of paresthesia in the affected region of the person's body. As the person moves, the stimulation electrodes may move toward or away from the nerve tissue being stimulated, thereby increasing or decreasing the intensity of the stimulating energy reaching the nerve fibers and ultimately the number of stimulated nerve fibers. This in turn affects the level and location of paresthesia in the affected region of the person's body. In some instances, such changes in the level and location of paresthesia experienced by the person may reduce the effectiveness of the stimulation, which is typically undesirable. For example, a person typically adjusts the level of stimulation to the nerve tissue to produce a stimulation paresthesia that covers the area of pain in the person's body, thereby reducing the overall level of pain experienced by the person. When the person then sits down, stands up, bends over or makes other physical movements that may change the location of the stimulation electrode with respect to the target nerve tissue, the person may experience a paresthesia that is less than optimal for relieving the person's pain. In addition, in certain situations, the electrodes may move closer to the target nerve tissue, which may cause the person to experience additional pain in the affected region.

SUMMARY OF THE INVENTION

The present invention provides systems and methods for controlling or regulating therapeutic nerve stimulation using electrical feedback.

In one embodiment, a stimulation system is provided for maintaining a constant level of paresthesia in a person's body. The stimulation system includes a stimulation lead, a stimulation source, a sensing device, and a controller. The stimulation source is operable to generate and transmit stimulation pulses. The stimulation lead is adapted for implantation into a person's body and comprises one or more stimulation electrodes adapted to be positioned proximate target nerve tissue in a nerve pathway, to receive the stimulation pulses form the stimulation source, and to deliver the stimulation pulses to the target nerve tissue to cause paresthesia in a portion of the person's body corresponding to the target nerve tissue. Each stimulation pulse induces an action potential in each of a plurality of stimulated nerve fibers within the nerve pathway. The sensing device is adapted for implantation into the person's body and comprises one or more sensing electrodes adapted to be positioned proximate the nerve pathway, to detect a compound action potential associated with each stimulation pulse, and to transmit one or more signals reflecting one or more detected compound action potentials. The compound action potential associated with each stimulation pulse comprises the action potentials of the plurality of nerve fibers within the nerve pathway that are stimulated by that stimulation pulse. The controller is operable to receive from the sensing device the one or more signals reflecting the one or more detected compound action potentials and to modify one or more stimulation parameters of the stimulation pulses generated by the stimulation source and delivered to the target nerve tissue by the one or more stimulation electrodes, based on the received one or more signals reflecting the one or more compound action potentials, to maintain a substantially constant level of paresthesia in the portion of the person's body corresponding to the target nerve tissue.

In another embodiment, a stimulation lead adapted for implantation in a person's body and to provide therapeutic stimulation of target nerve tissue within the person's body is provided. The stimulation lead includes one or more stimulation electrodes and one or more sensing electrodes. The one or more stimulation electrodes are adapted to be positioned proximate target nerve tissue in a nerve pathway and to deliver stimulation pulses to the target nerve tissue to cause paresthesia in a portion of the person's body corresponding to the target nerve tissue. Each stimulation pulse induces an action potential in each of a plurality of stimulated nerve fibers within the nerve pathway. The one or more sensing electrodes are located on the stimulation lead at a distance from the stimulation electrodes and adapted to be positioned proximate the nerve pathway, to detect a compound action potential associated with each stimulation pulse, and to transmit one or more signals reflecting one or more detected compound action potentials. The compound action potential associated with each stimulation pulse comprises the action potentials of the plurality of nerve fibers within the nerve pathway that are stimulated by that stimulation pulse.

Particular embodiments of the present invention may provide one or more technical advantages. For example, in certain embodiments, a stimulation system includes sensing electrodes, capable of detecting compound action potentials of a number of stimulated nerve fibers in target nerve tissue within a person's body, and a controller, capable of adjusting the stimulation pulses applied to the target nerve tissue based at least on the amplitude of one or more of the detected compound action potentials to maintain a substantially constant level of paresthesia in an affected region of the person's body. Thus, when the stimulation electrodes move with respect to the target nerve tissue (such as when the person moves), which affects the number of stimulated nerve fibers and thus the amplitude of the compound action potentials, the controller adjusts one or more stimulation parameters, the amplitude (or intensity) and/or pulse width for example, of the stimulation pulses applied to the target nerve tissue by the stimulation electrodes to maintain a substantially constant level of paresthesia in the affected region of the person's body. As a result, the likelihood of the person experiencing discomfort due to excessively intense stimulation due to movement of the stimulation electrodes toward the target nerve tissue, or experiencing their underlying pain or otherwise experiencing insufficient relief in the affected region of the person's body due to insufficiently intense stimulation due to movement of the stimulation electrodes away from the target nerve tissue, may be substantially reduced or eliminated.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which.

DESCRIPTION OF EXAMPLE EMBODIMENTS

According to the present invention, an electrical stimulation system is used to control or regulate electrical stimulation of target nerve tissue in the spinal cord, a peripheral nerve, or other nerve in the body to cause a substantially constant level of paresthesia in an affected region of a person's body. In particular, an electrical stimulation lead having a number of stimulation electrodes is implanted inside the person's body such that the stimulation electrodes are located proximate the target nerve tissue. For example, the stimulation lead may be implanted within a person's epidural space for stimulating target nerve tissue in the person's spinal cord. The electrodes deliver electrical stimulation pulses to the target nerve tissue, which induces an action potential in individual nerve fibers in the target nerve tissue and causes paresthesia in an affected region of a person's body corresponding to the target nerve tissue. Sensing electrodes located near the spinal cord at some distance from the stimulation electrodes detect the sum or other aggregation of these action potentials, which may be referred to as a compound action potential. The sensing electrodes transmit signals reflecting the detected compound action potentials to a controller which uses the signals to control or regulate one or more stimulation parameters, the amplitude (or intensity) and/or pulse width for example, of the electrical stimulation pulses applied to the target nerve tissue via the stimulation electrodes to maintain a substantially constant level of paresthesia in the affected region of the person's body.

FIGS. 1A-1D illustrate example electrical stimulation systems 10 for controlling or regulating therapeutic nerve stimulation in a person's body using electrical feedback. Stimulation system 10 generates and applies electrical stimulation pulses to target nerve tissue in a nerve pathway within the person's body. In certain embodiments, stimulation system 10 generates and applies an electrical stimulus to target nerve tissue in the person's spinal cord to produce paresthesia in a region of the person's body corresponding to the stimulated target nerve tissue of the spinal cord. In other embodiments, stimulation system 10 generates and applies an electrical stimulus to target nerve tissue in a peripheral nerve, a root nerve, a cranial nerve, the brainstem, or any other suitable nerve in the person's body to produce paresthesia in a region of the person's body corresponding to the stimulated target nerve tissue.

Stimulation system 10 includes an implantable electrical stimulation source 12, an implantable electrical stimulation lead 14, an implantable sensing device 15, and a controller 18. In operation, each of stimulation source 12, stimulation lead 14, and sensing device 15 are implanted inside the person's body, as discussed in greater detail below. Controller 18 may be implanted inside or located outside the person's body depending on the particular implementation of stimulation system 10.

Stimulation source 12 is coupled to a connecting portion 20 of stimulation lead 14. Electrical stimulation lead 14 includes one or more stimulation electrodes 22 located in a stimulating portion 24 of stimulation lead 14. Stimulation lead 14 is adapted to be implanted such that stimulation electrodes 22 are located proximate the target nerve tissue. Stimulation source 12 produces electrical stimulation pulses that are transmitted via connecting portion 20 to stimulation electrodes 22, which deliver the electrical stimulation pulses to target nerve tissue in a nerve pathway to cause paresthesia in a region of the person's body corresponding to the target nerve tissue. Each electrical stimulation pulse provides a pulse of electrical energy.

In certain embodiments, stimulation source 12 may produce electrical stimulation pulses according to one or more stimulation programs, each including a number of stimulation sets. Each stimulation set may specify a number of stimulation parameters for that stimulation set. Stimulation parameters may include, for example, an amplitude (or intensity), a frequency, phase information, and a pulse width for each of a series of stimulation pulses that stimulation electrodes 22 are to deliver to the target nerve tissue during a particular time interval, along with a polarity for each stimulation electrode 22 during each stimulation pulse. Stimulation parameters may also include a pulse shape, for example, biphasic cathode first, biphasic anode first, or any other suitable pulse shape. Various stimulation programs, stimulation sets and stimulation parameters associated with the electrical stimulation pulses produced by stimulation source 12 are discussed in greater detail below with reference to FIGS. 6-8.

Sensing device 15 includes one or more sensing electrodes 26 and is adapted to be implanted such that sensing electrodes 26 are located at some distance along the nerve pathway from stimulation electrodes 22. Sensing electrodes 26 are operable to detect action potentials produced in the nerve fibers in the nerve pathway by the electrical stimulation pulses applied to the target nerve tissue by stimulation electrodes 22. In certain embodiments, sensing electrodes are operable to detect the compound action potential of a number of nerve fibers stimulated by each electrical stimulation pulse delivered by stimulation electrodes 22, and to transmit one or more signals reflecting each detected compound action potential to controller 18. As discussed below, sensing device 15 may be physically integrated with stimulation lead 14 or may be a physically distinct apparatus. For example, in some embodiments, sensing device 15 includes one or more sensing electrodes 26 located on stimulation lead 14 at some distance from stimulation electrodes 22. In other embodiments, sensing device 15 includes a sensing lead 16 that includes one or more sensing electrodes 26 and that is physically distinct from stimulation lead 14.

Controller 18 controls or regulates one or more stimulation parameters of the electrical stimulation pulses generated by stimulation source 12 and delivered to the target nerve tissue by stimulation electrodes 22 based at least on the compound action potentials detected by sensing electrodes 26. Stimulation parameters are discussed in greater detail below with reference to FIGS. 6-8.

Stimulation system 10 may be partially or completely implanted into the person's body, as discussed in greater detail below. In particular, stimulation lead 14 may be implanted such that stimulation electrodes 22 are located proximate target nerve tissue to produce paresthesia in a region of the person's body corresponding to the target nerve tissue. Sensing device 15, which may or may not be integrated with stimulation lead 14, may be implanted such that sensing electrodes 24 are located proximate the nerve pathway at some distance along the nerve pathway from stimulation electrodes 22. In addition, in certain embodiments, sensing electrodes 26 are located at a sufficient distance from stimulation electrodes 22 along the nerve pathway such that the stimulus artifact caused by each electrical stimulation pulse delivered to the target nerve tissue by stimulation electrodes 22 has substantially or completely occurred by the time the compound action potential is detected by sensing electrodes 26. Thus, the stimulus artifact associated with each electrical stimulation pulse does not affect, at least not significantly, the compound action potentials detected by sensing electrodes 26.

Figure 1A:
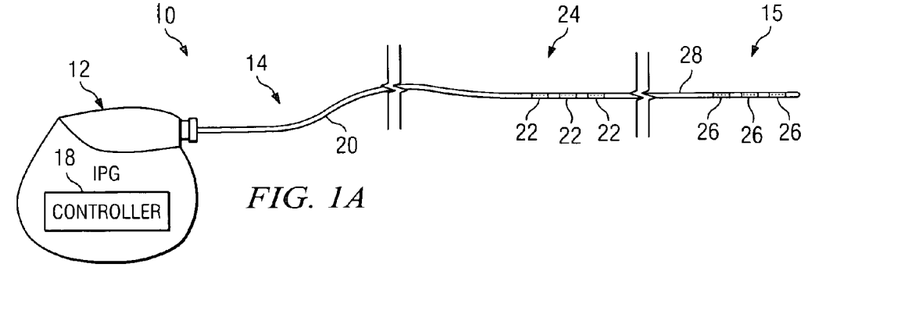
FIGS. 1A-1D illustrate example stimulation systems for controlling or regulating therapeutic nerve stimulation in a person's body using electrical feedback.

In the embodiment shown in FIG. 1A, stimulation source 12 includes an implantable pulse generator (IPG) integrated with controller 18. An example IPG may be one manufactured by Advanced Neuromodulation Systems, Inc., such as the Genesis® System, part numbers 3604, 3608, 3609, and 3644. Sensing electrodes 26 are located on stimulation lead 14 and are separated from stimulation electrodes 22 by a connecting portion 28 of stimulation lead 14. Both sensing electrodes 26 and stimulation electrodes 22 are electrically connected to stimulation source 12 by wires running within, or integrated into, stimulation lead 14. As discussed above, stimulation lead 14 is implanted into the person's body such that stimulation electrodes 22 are located proximate the target nerve tissue in the nerve pathway and sensing electrodes 26 are located at some distance along the nerve pathway from stimulation electrodes 22.

In operation, stimulation source 12 generates and transmits electrical stimulation pulses to stimulation electrodes 22, which deliver the electrical stimulation pulses to the target nerve tissue. Each electrical stimulation pulse induces an action potential in one or more nerve fibers within the nerve pathway that are stimulated by the stimulation pulse. The action potentials travel through these nerve fibers along the nerve pathway. As the action potentials generated by an electrical stimulation pulse pass by sensing electrodes 26, sensing electrodes 26 detect a compound action potential for the group of nerve fibers stimulated by that stimulation pulse. The compound action potential is the sum or other aggregation of the action potentials within each of the stimulated nerve fibers.

Sensing electrodes 26 may transmit one or more signals, each reflecting one or more detected compound action potentials, to controller 18. Sensing electrodes 26 may transmit one or more signals reflecting each detected compound action potential detected by sensing electrodes 26, or one or more signals reflecting a group of detected compound action potentials associated with a group of electrical stimulation pulses. For example, in certain embodiments, each sensing electrode 26 may individually detect a compound action potential associated with each electrical stimulation pulse and transmit to controller 18 a signal reflecting that compound action potential or a signal reflecting multiple compound action potentials for multiple stimulation pulses. In certain other embodiments, some or all of the sensing electrodes 26 may collectively detect a compound action potential associated with each electrical stimulation pulse and collectively transmit to controller 18 a signal reflecting that compound action potential or a signal reflecting multiple compound action potentials for multiple stimulation pulses. In certain embodiments, signals reflecting a compound action potential associated with an electrical stimulation pulse may have an amplitude or other value that reflects the compound action potential of the group of nerve fibers stimulated by that electrical stimulation pulse. The value may be the compound action potential itself or may be generated to reflect the compound action potential. The present invention contemplates any signals to reflect compound action potentials associated with electrical stimulation pulses. Sensing electrodes 26 may transmit the one or more signals, each reflecting one or more detected compound action potentials, to controller 18 via one or more wires running within, or integrated into, stimulation lead 14.

Controller 18 analyzes the signals reflecting the compound action potentials received from sensing electrodes 26 and, if appropriate, adjusts one or more stimulation parameters of the electrical stimulation pulses generated by stimulation source 12 and delivered to the target nerve tissue by stimulation electrodes 22 to maintain a substantially constant level of paresthesia in the affected region of the person's body. For example, if the amplitude of the compound action potentials detected by sensing electrodes 26 decreases, controller 18 may increase the amplitude (or intensity) and/or pulse width of electrical stimulation pulses generated by stimulation source 12 to maintain a substantially constant level of paresthesia for the person. As another example, if the amplitude of the compound action potentials detected by sensing electrodes 26 increases, controller 18 may decrease the amplitude (or intensity) and/or pulse width of electrical stimulation pulses generated by stimulation source 12 to maintain a substantially constant level of paresthesia for the person. As a result, the likelihood of the person experiencing discomfort due to excessively intense stimulation due to movement of stimulation electrodes 22 toward the target nerve tissue, or experiencing their underlying pain or otherwise experience insufficient relief in the affected region of the person's body due to insufficiently intense stimulation due to movement of stimulation electrodes 22 away from the target nerve tissue, may be substantially reduced or eliminated.

Controller 18 may determine whether to adjust one or more stimulation parameters of the electrical stimulation pulses generated by stimulation source 12 based on one or more signals, each reflecting compound action potentials associated with one or more electrical stimulation pulses. For example, controller 18 may determine whether to adjust one or more stimulation parameters based on a particular signal reflecting a single compound action potential, a particular signal reflecting multiple compound action potentials, multiple signals reflecting a single compound action potential, multiple signals reflecting multiple compound action potentials, or otherwise based on one or more compound action potentials.

In certain embodiments, controller 18 may adjust one or more stimulation parameters of the electrical stimulation pulses generated by stimulation source 12 if one or more signals received from sensing electrodes 26 indicate that the amplitude of the compound action potentials detected by sensing electrodes 26 crosses one or more predetermined threshold values to maintain a substantially constant level of paresthesia in the portion of the person's body corresponding to the target nerve tissue. For example, controller 18 may increase the amplitude (or intensity) and/or pulse width of the electrical stimulation pulses generated by stimulation source 12 if one or more signals received from sensing electrodes 26 indicate that the amplitude of one or more compound action potentials detected by sensing electrodes 26 increases above a predefined upper threshold. Similarly, controller 18 may decrease the amplitude (or intensity) and/or pulse width of the electrical stimulation pulses generated by stimulation source 12 if one or more signals received from sensing electrodes 26 indicate that the amplitude of one or more compound action potentials detected by sensing electrodes 26 decreases below a predefined lower threshold. One or more of the threshold values used by controller 18, such as the upper and lower threshold values discussed above for example, may be pre-programmed by the person using stimulation system 10 or by another user, such as a doctor. In certain embodiments, one or more of the threshold values used by controller 18 may be adjusted by the person using stimulation system 10 or by another user, such as a doctor, during the operation of stimulation system 10. In addition, in certain embodiments, one or more of such threshold values (such as the upper and lower threshold values, for example) may have the same or different amplitudes, as appropriate, to help avoid hysteresis.

Figure 1B:
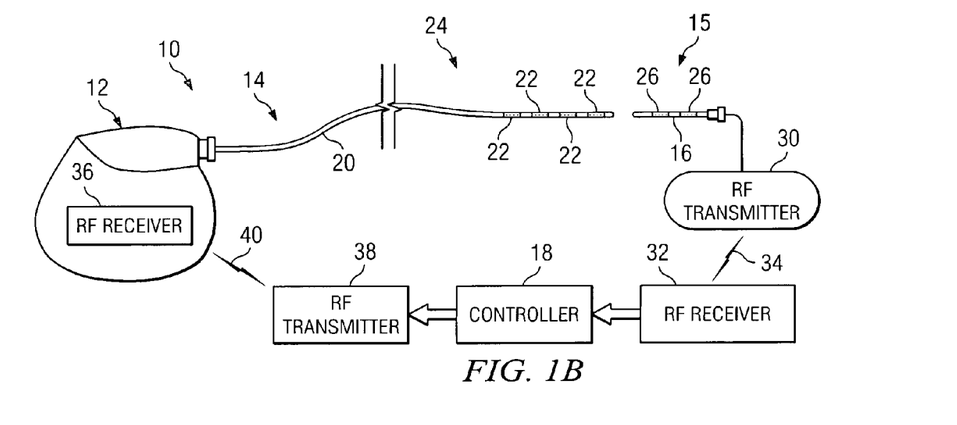

In the embodiment shown in FIG. 1B, sensing device 15 includes a sensing lead 16 distinct from stimulation lead 14. Stimulation lead 14 and sensing lead 16 are adapted to be implanted into a person's body such that stimulation electrodes 22 are located proximate target nerve tissue in a nerve pathway and sensing electrodes 26 are located at some distance along the nerve pathway from stimulation electrodes 22. A first wireless transmitter 30 coupled to sensing lead 16 is implanted within the person's body. A first wireless receiver 32 located external to the person's body is capable of receiving wireless signals from first wireless transmitter 30. First wireless receiver 32 is coupled to controller 18, which is also located external to the person's body. The wireless signals transmitted by first wireless transmitter 30 are represented in FIG. 1B by wireless link symbol 34. An example first wireless transmitter 30 may be one manufactured by Advanced Neuromodulation Systems, Inc., such as the Renew® System, part numbers 3508 and 3516. An example first wireless receiver 32 may be one manufactured by Advanced Neuromodulation Systems, Inc., such as the Renew® System, part numbers 3408 and 3416.

Stimulation source 12 includes an implantable second wireless receiver 36, which may be similar or identical to first wireless receiver 32. Second wireless receiver 36 is capable of receiving wireless signals from a second wireless transmitter 38 located external to the person's body and coupled to controller 18. The wireless signals transmitted by second wireless transmitter 38 are represented in FIG. 1B by wireless link symbol 40. Second wireless transmitter 38 may be similar or identical to first wireless transmitter 30, and may or may not be integrated with controller 18.

In operation, stimulation source 12 generates and transmits electrical stimulation pulses to stimulation electrodes 22 for delivery to the target nerve tissue. The stimulation pulses induce action potentials in various nerve fibers in the nerve pathway, as discussed above. Sensing electrodes 26 detect compound action potentials of the nerve fibers stimulated by the stimulation pulse, as discussed above. Sensing electrodes 26 transmit signals reflecting the detected compound action potentials to first wireless transmitter 30, which transmits the signals to first wireless receiver 32 via wireless link 34.

Controller 18 analyzes the signals received by wireless receiver 32 and determines and/or adjusts one or more stimulation parameters for the electrical stimulation pulses generated by stimulation source 12 based on one or more of the received signals, each reflecting one or more detected compound action potentials, to maintain a substantially constant level of paresthesia in the affected region of the person's body. Controller 18 transmits these determined and/or adjusted stimulation parameters, along with power for generating electrical stimulation pulses, from second wireless transmitter 38 to second wireless receiver 36 via wireless link 40. Using the power received from controller 18 at second wireless receiver 36, stimulation source 12 generates electrical stimulation pulses according to the stimulation parameters received from controller 18 at second wireless receiver 36 such that a substantially constant level of paresthesia is maintained in the affected region of the person's body.

Figure 1C:
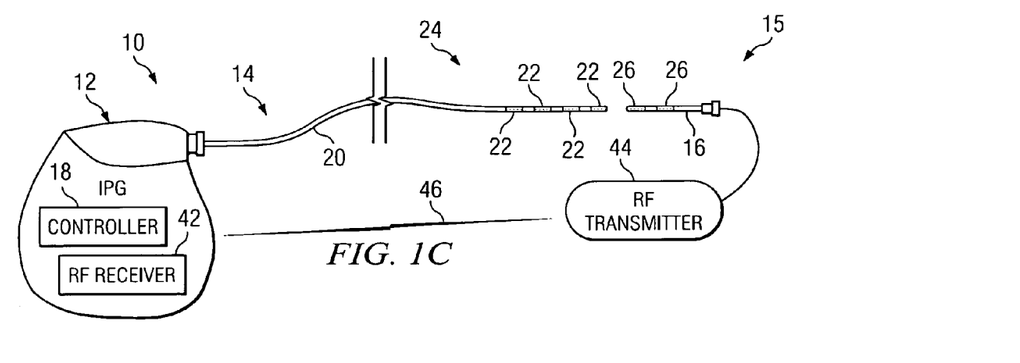

In the embodiment shown in FIG. 1C, stimulation source 12 includes controller 18 as well as an implantable wireless receiver 42, which may be similar to wireless receivers 32 and/or 36 described above. An implantable wireless transmitter 44, which may be similar to wireless transmitter 30 and/or 38 described above, is coupled to sensing lead 16 and capable of transmitting wireless signals to wireless receiver 42 via a wireless link 46.

In operation, stimulation source 12 generates and transmits electrical stimulation pulses to stimulation electrodes 22, which deliver the electrical stimulation pulses to the target nerve tissue, which in turn induce action potentials in various nerve fibers in the nerve pathway, as discussed above. Sensing electrodes 26 detect the compound action potential of the nerve fibers stimulated by each stimulation pulse, as discussed above. The detected compound action potentials are transmitted from wireless transmitter 42 to wireless receiver 44 via wireless link 46, and are used by controller 18 to control or regulate one or more stimulation parameters of the electrical stimulation pulses generated by stimulation source 12 to maintain a substantially constant level of paresthesia in the affected region of the person's body.

Figure 1D:
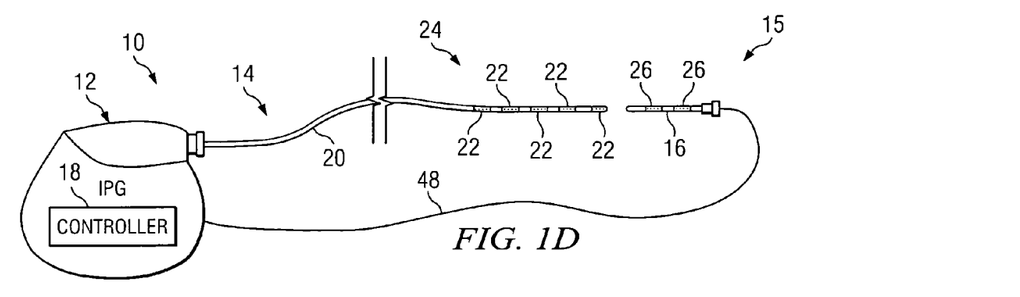
Figure 2A:
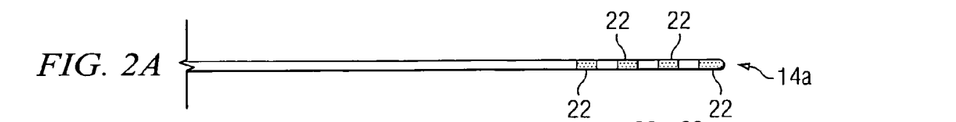
FIGS. 2A-2I illustrate example stimulation leads.
Figure 2B:
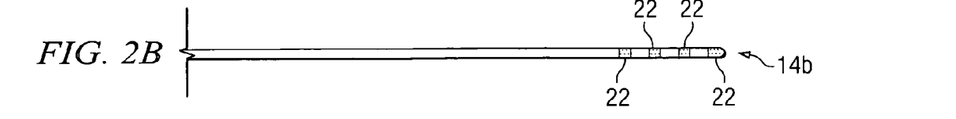
Figure 2C:
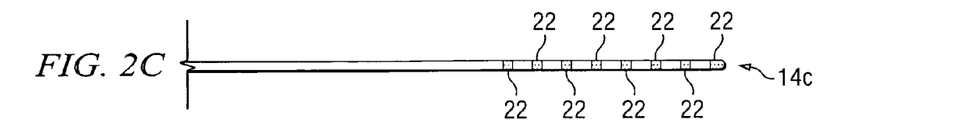
Figure 2D:
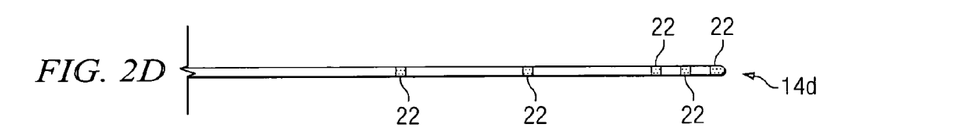
Figure 2E:
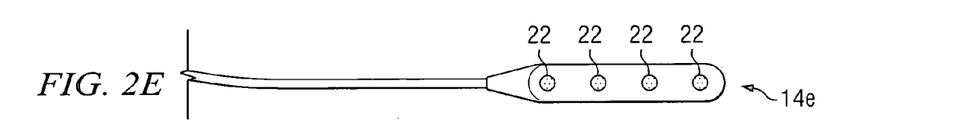
Figure 2F:
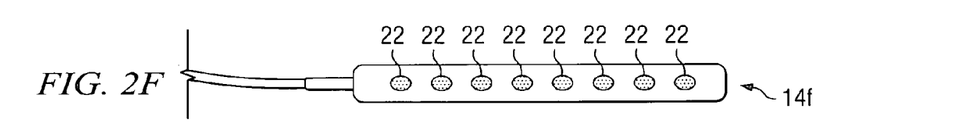
Figure 2G:
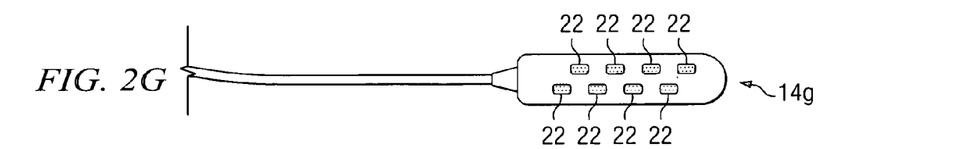
Figure 2H:
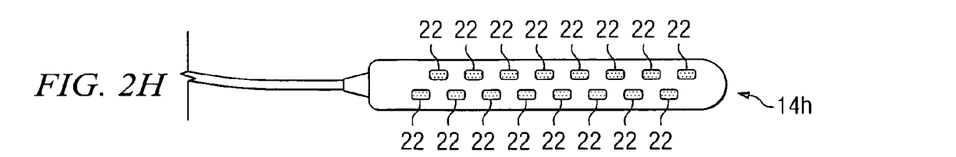
Figure 2I:
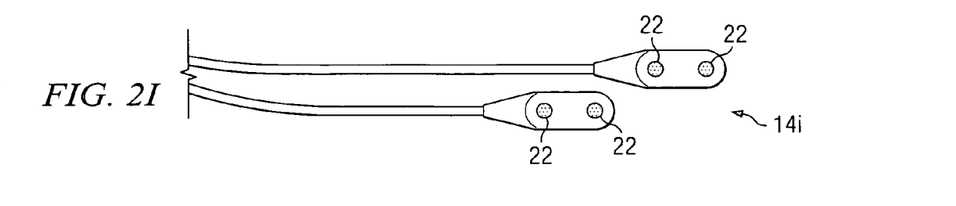
Figure 3A:
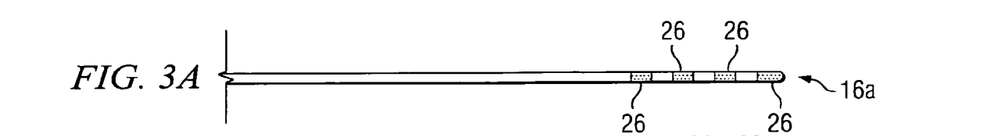
FIGS. 3A-3I illustrate example sensing leads.
Figure 3B:
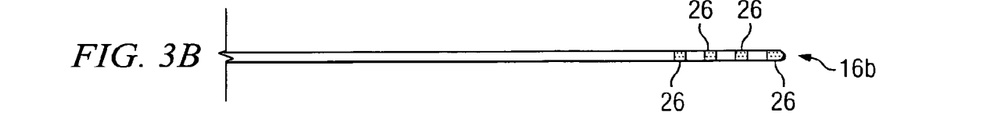
Figure 3C:
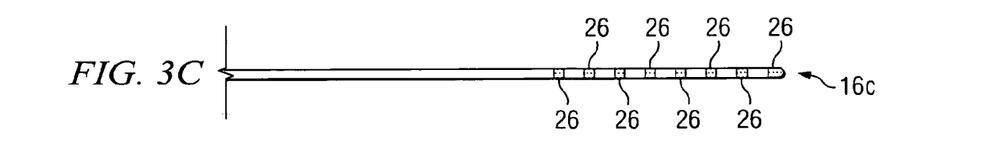
Figure 3D:
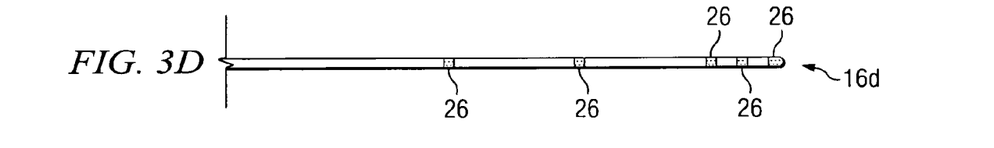
Figure 3E:
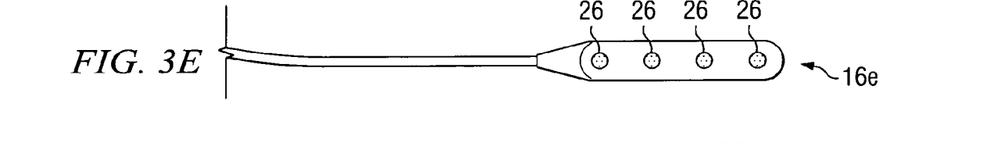
Figure 3F:
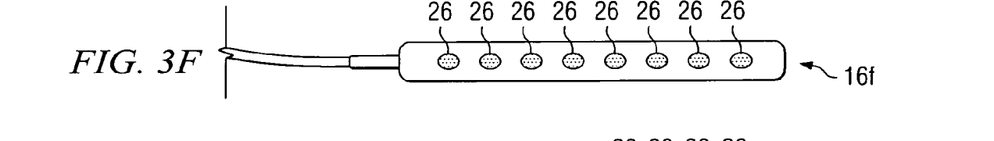
Figure 3G:
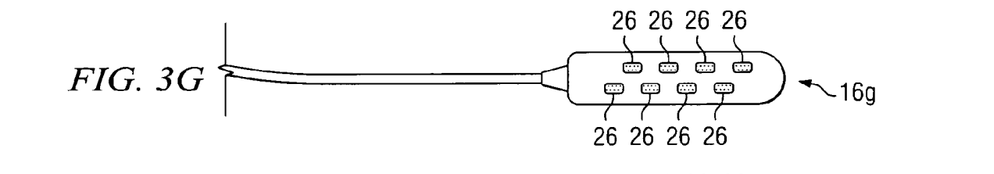
Figure 3H:
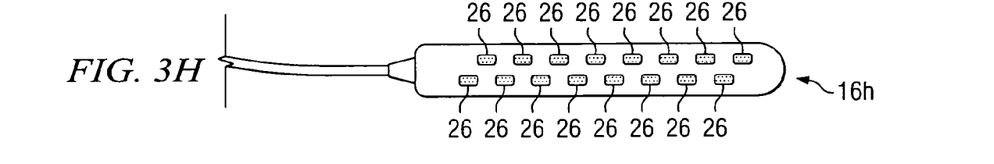
Figure 3I:
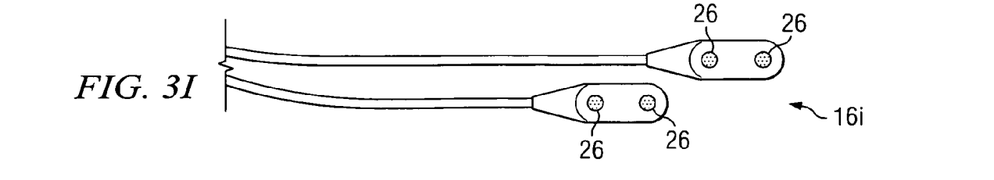
Figure 4A:
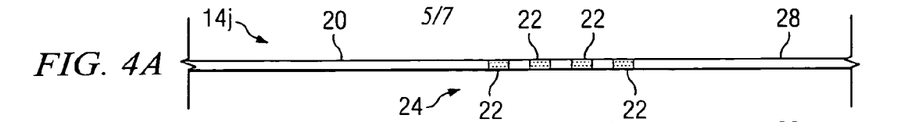
FIGS. 4A-4I illustrate example stimulation leads that include both stimulation electrodes and sensing electrodes.
Figure 4B:
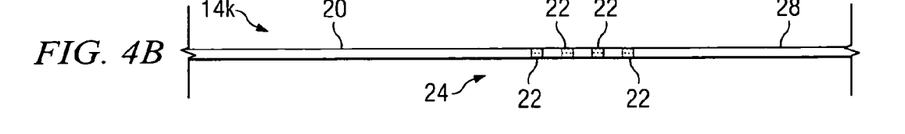
Figure 4C:
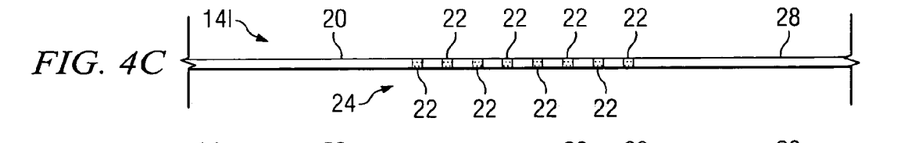
Figure 4D:
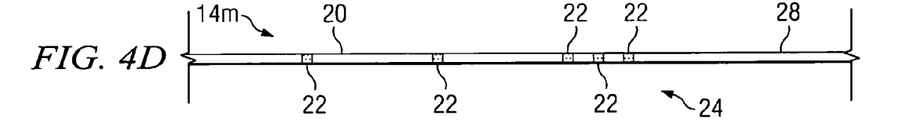
Figure 4E:
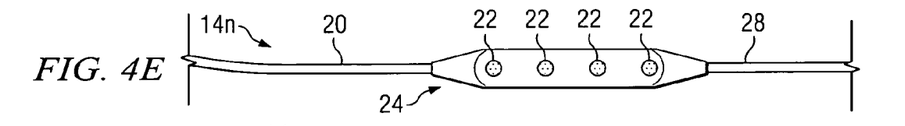
Figure 4F:
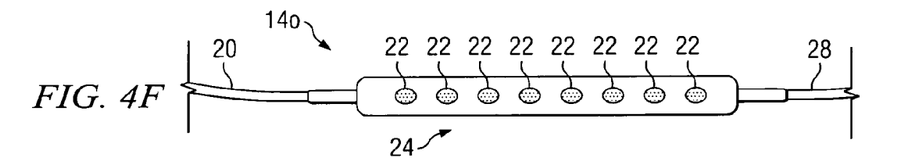
Figure 4G:
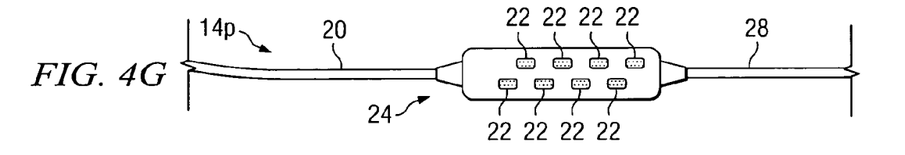
Figure 4H:
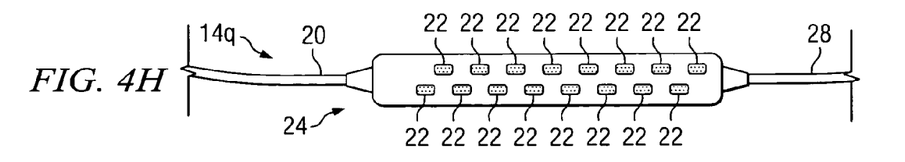
Figure 4I:
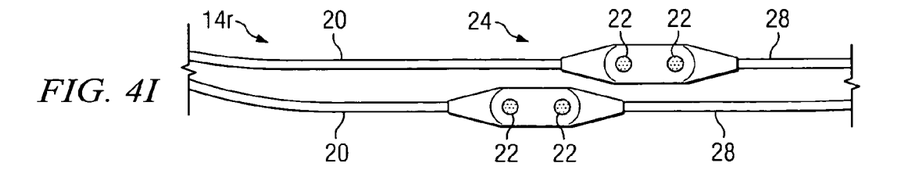

In the embodiment shown in FIG. 1D, sensing lead 16 is connected to controller 18 by a wire 48 implanted within the person's body. In operation, the compound action potentials detected by sensing electrodes 26 are transmitted to controller 18 via wire 48.

It should be understood that the embodiments shown in FIGS. 1A through 1D are merely examples, and other embodiments may include any suitable combinations of the features shown in FIGS. 1A through 1D. In addition, in some embodiments in which controller 18 is located external to the person's body, such as shown in FIG. 1B, controller 18 may include an interface that may be used by a doctor, the patient, or another user to adjust or otherwise manage the operation of stimulation system 10. For example, a doctor may manually adjust the duration, amplitude (or intensity), pulse width, frequency, or pattern of electrical stimulation pulses to be generated by stimulation source 12.

FIGS. 2A-2I illustrate example stimulation leads 14 that may be used in certain embodiments of stimulation system 10 in which sensing device 15 is distinct from stimulation lead 14. As described above, each stimulation lead 14 includes one or more stimulation electrodes 22 adapted to be positioned near the target nerve tissue and to deliver electrical stimulation pulses received from stimulation source 12 to the target nerve tissue. In certain embodiments, stimulation electrodes 22 are macroelectrodes. However, stimulation electrodes 22 may be any type of electrode suitable for emitting electrical energy. A percutaneous stimulation lead 14, such as example stimulation leads 14a-d, includes one or more circumferential stimulation electrodes 22 spaced apart from one another along the length of stimulation lead 14. Circumferential stimulation electrodes 22 emit electrical stimulation energy generally radially in all directions. A laminotomy or paddle stimulation lead 14, such as example stimulation leads 14e-i, includes one or more directional stimulation electrodes 22 spaced apart from one another along one surface of stimulation lead 14. Directional stimulation electrodes 22 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, two or more stimulation leads 14 may be used in combination.

FIGS. 3A-3I illustrate example sensing leads 16 that may be used in certain embodiments of stimulation system 10. As discussed above, each sensing lead 16 includes one or more sensing electrodes 26 adapted to be positioned at some distance along the same nerve pathway as stimulation electrodes 22 and capable of: (1) detecting action potentials in nerve fibers within the nerve pathway that are stimulated by electrical stimulation pulses delivered by stimulation electrodes 22, and (2) transmitting signals reflecting such detected compound action potentials to controller 18. In certain embodiments, sensing electrodes 26 are microelectrodes or semi-microelectrodes. However, sensing electrodes 26 may be any type of electrode suitable for detecting electrical energy. A percutaneous sensing lead, such as example sensing leads 16a-d, includes one or more circumferential sensing electrodes 26 spaced apart from one another along the length of sensing lead 16. Circumferential sensing electrodes 26 detect electrical energy generally radially in all directions. A laminotomy or paddle sensing lead 16, such as example sensing leads 16e-i, includes one or more directional sensing electrodes 26 spaced apart from one another along one surface of sensing lead 16. Directional sensing electrodes 26 detect electrical energy in a direction generally perpendicular to the surface of sensing lead 16 on which they are located. Although various types of sensing leads 16 are shown as examples, the present invention contemplates stimulation system 10 including any suitable type of sensing lead 16 in any suitable number. In addition, two or more sensing leads 16 may be used in combination.

FIGS. 4A-4I illustrate example stimulation leads 14 that include both stimulation portion 24, which includes stimulation electrodes 22, and sensing device 15, which includes sensing electrodes 26. Stimulation leads 14j-r are similar to leads 14a-i illustrated in FIGS. 2A-2I, but extend beyond stimulating portion 24 toward the not-illustrated sensing device 15, which is coupled to stimulating portion 24 by connecting portion 28. Each stimulation lead 14j-r may include any suitable type of sensing device 15, such as the various percutaneous or paddle leads shown in FIGS. 3A-3I, for example. Thus, stimulation leads 14j-r may include any suitable combination and orientation of stimulation electrodes 22 and sensing electrodes 26.

In certain embodiments, stimulation leads 14j-r may include macroelectrode stimulation electrodes 22 and semi-microelectrode sensing electrodes 26. However, as discussed above, stimulation electrodes 22 may include any type of electrodes suitable for emitting electrical energy and sensing electrodes 26 may include any type of electrodes suitable for detecting electrical energy.

Stimulation system 10 may include any one or more of the leads shown in FIGS. 2A-2I, 3A-3I, and 4A-4I, singly or in any suitable combination. For example, in certain embodiments, the configuration of system 10 shown in FIG. 1A may include any of the stimulation leads 14 shown in FIGS. 4A-4I. As another example, in certain embodiments, the configurations of system 10 shown in FIGS. 1B-1D may include any combination of the stimulation leads 14 shown in FIGS. 2A-2I and the sensing leads 16 shown in FIGS. 3A-3I.

Figure 5:
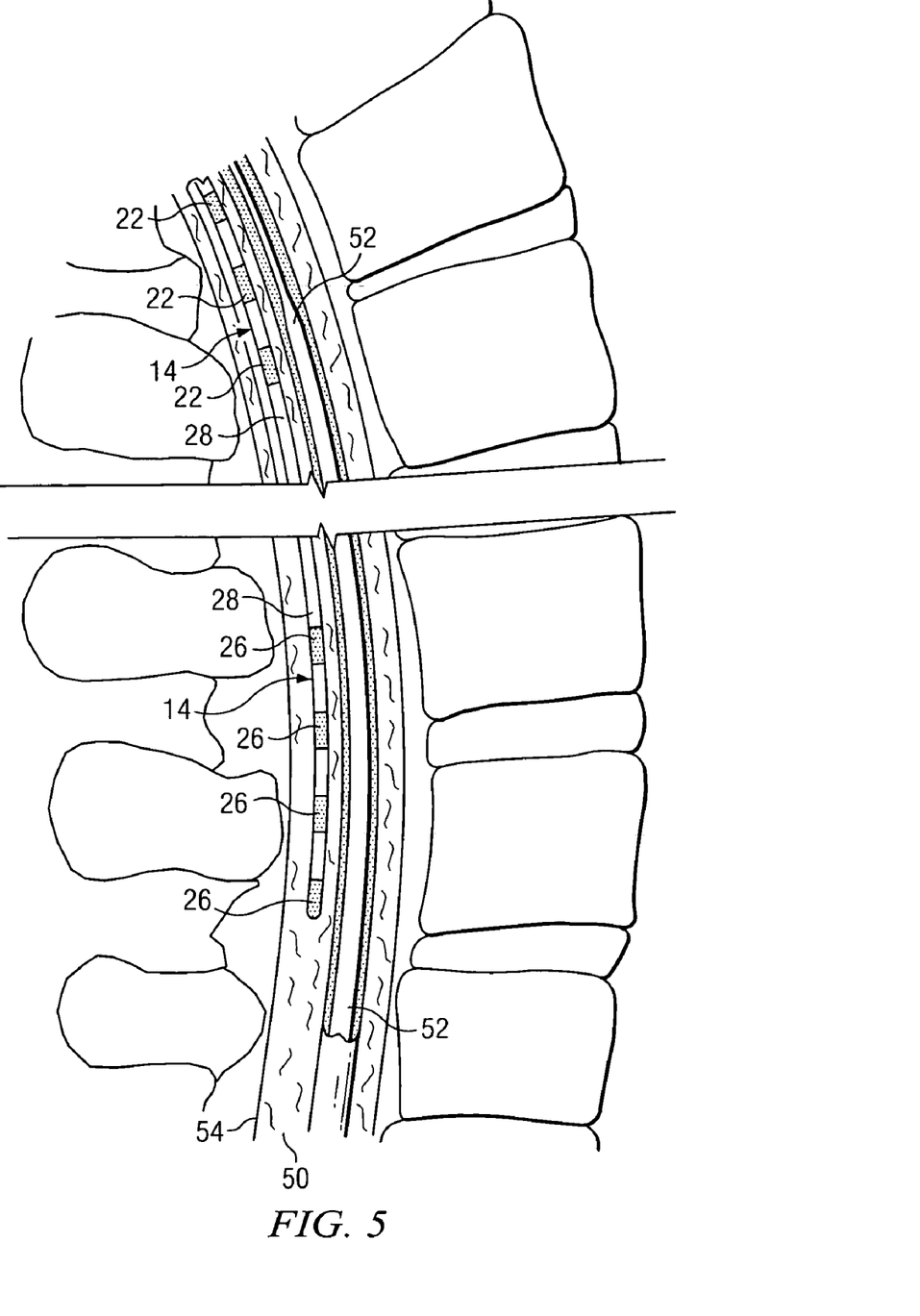
FIG. 5 illustrates the stimulation lead of the stimulation system of FIG. 1A implanted in the epidural space proximate a person's spinal cord.

FIG. 5 illustrates an example of the stimulation lead 14 of FIG. 1A implanted in a person's epidural space 50 proximate the person's spinal cord 52. The person's ligamentum flavum 54 is also shown. In this example, both stimulation electrodes 22 and sensing electrodes 26 are circumferential electrodes located along the longitudinal axis of a percutaneous stimulation lead 14. Stimulation electrodes 22 are located proximate target nerve tissue in spinal cord 52, while sensing electrodes 26 are located proximate spinal cord 52 at some distance along spinal cord 52 from stimulation electrodes 22.

Other components of stimulation system 10 may be implanted at various locations within the person's body. For example, stimulation source 12 may be implanted within a subcutaneous pocket within the person's torso (such as in or near the chest or buttocks), and connecting portion 20 may be tunneled, at least in part, subcutaneously underneath the person's skin to connect stimulation source 12 with stimulation lead 14. However, stimulation source 12 may be located at any suitable location within the person's body according to particular needs.

Figure 6:
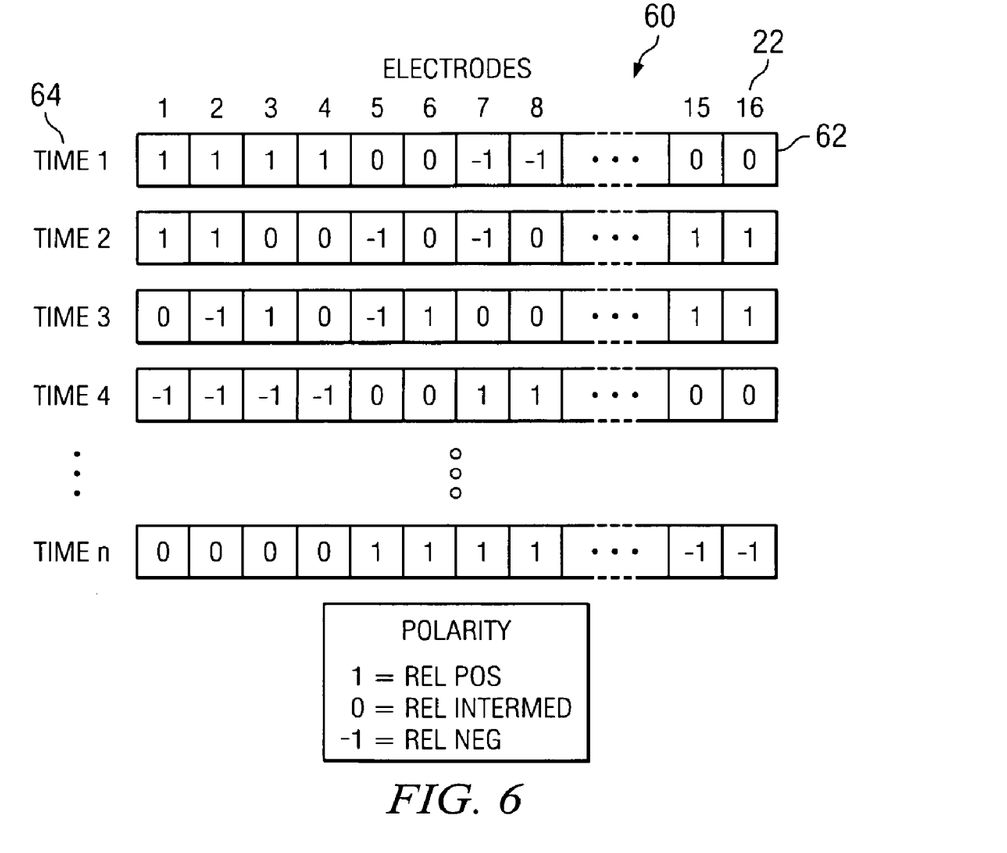
FIG. 6 illustrates an example stimulation set.

FIG. 6 illustrates an example stimulation set 60. One or more stimulation sets 60 may be provided, each stimulation set 60 specifying a number of stimulation parameters for the stimulation set 60. For example, as described more fully below with reference to FIGS. 7-8, multiple stimulation sets 60 may be executed in a suitable sequence according to a pre-programmed or randomized stimulation program. Example stimulation parameters for a stimulation set 60 may include an amplitude (or intensity), a frequency, phase information, and a pulse width for each of a series of stimulation pulses that stimulation electrodes 22 are to deliver to the target nerve tissue during a time interval during which stimulation set 60 is executed, along with a polarity 62 for each stimulation electrode 22 within each stimulation pulse. In general, in particular embodiments in which electrical stimulation lead 14 includes two or more stimulation electrodes 22, electric fields are generated between adjacent stimulation electrodes 22 having different polarities 62 to deliver electrical stimulation pulses to the target nerve tissue. In particular embodiments in which electrical stimulation lead 14 includes a single stimulation electrode 22, such as a single stimulation electrode 22 at the tip of stimulation lead 14 for example, electric fields are generated between the single stimulation electrode 22 and a terminal or other electrical contact associated with stimulation source 12. Stimulation parameters may also include a pulse shape, for example, biphasic cathode first, biphasic anode first, or any other suitable pulse shape. Stimulation parameters are not limited to the preceding but may include any suitable parameters known to those skilled in the art.

The polarity for a stimulation electrode 22 at a time 64 beginning a corresponding stimulation pulse or sub-interval within a stimulation pulse may be a relatively positive polarity 62, a relatively negative polarity 62, or an intermediate polarity 62 between the relatively positive polarity 62 and relatively negative polarity 62. For example, the relatively positive polarity 62 may involve a positive voltage, the relatively negative polarity 62 may involve a negative voltage, and the relatively intermediate polarity 62 may involve a zero voltage (i.e. "high impedance"). As another example, the relatively positive polarity 62 may involve a first negative voltage, the relatively negative polarity 62 may involve a second negative voltage more negative than the first negative voltage, and the relatively intermediate polarity 62 may involve a negative voltage between the first and second negative voltages. The availability of three distinct polarities 62 for a stimulation electrode 22 may be referred to as "tri-state" electrode operation. The polarity 62 for each stimulation electrode 22 may change for each of the sequence of times 64 corresponding to stimulation pulses or to sub-intervals within a stimulation pulse according to the stimulation parameters specified for the stimulation set 60. For example, as is illustrated in FIG. 6 for an example stimulation set 60 for a stimulation lead 14 with sixteen stimulation electrodes 22, the polarities 62 of the sixteen stimulation electrodes 22 may change for each of the sequence of times 64. In the example of FIG. 6, a relatively positive polarity 62 is represented using a "1," a relatively intermediate polarity 62 is represented using a "0," and a relatively negative polarity 62 is represented using a "−1," although any values or other representations may be used.

Figure 7:
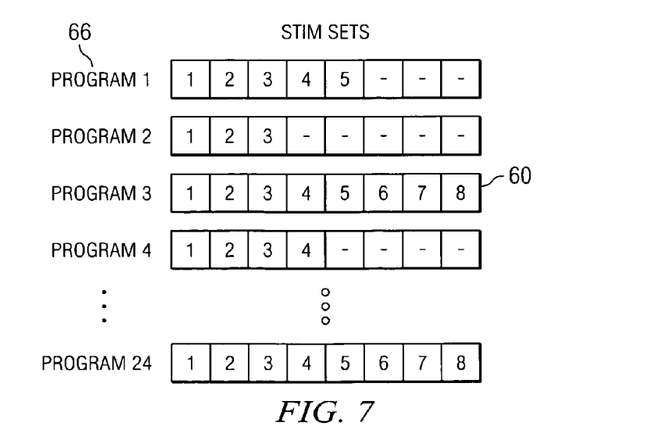
FIG. 7 illustrates a number of example stimulation programs, each of which includes a number of stimulation sets.
Figure 8:
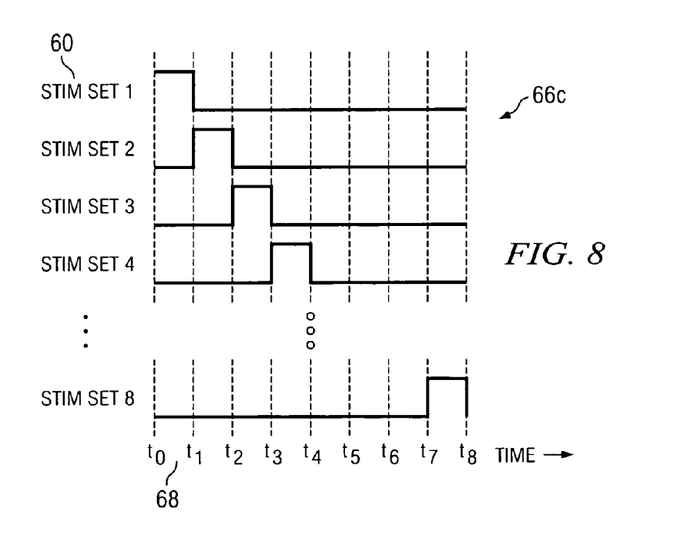
FIG. 8 illustrates example execution of a sequence of stimulation sets within an example stimulation program.

FIG. 7 illustrates a number of example stimulation programs 66, each including a number of stimulation sets 60. One or more simulation programs 66 may be set up to provide electrical stimulation of the target nerve tissue. As described above, each stimulation set 60 specifies a number of stimulation parameters for the stimulation set 60. In one embodiment, within each stimulation program 66, stimulation system 10 consecutively executes the sequence of one or more stimulation sets 60 associated with stimulation program 66. The sequence may be executed only once, repeated a specified number of times, or repeated an unspecified number of times within a specified time period. For example, as is illustrated in FIG. 8 for the third example stimulation program 66c including eight stimulation sets 60, each of the eight stimulation sets 60 is consecutively executed in sequence. Although the time intervals 68 ($t_1$-$t_0$, $t_2$-$t_1$, etc.) during which the stimulation sets 60 are executed are shown as being equal, the present invention contemplates a particular stimulation set 60 being executed over a different time interval 68 than one or more other stimulation sets 60 according to particular needs.

Although stimulation system 10 is illustrated for example as accommodating up to twenty-four stimulation programs 66 each including up to eight stimulation sets 60, the present invention contemplates any number of stimulation programs 66 each including any number of stimulation sets 60. For example, in a very simple case, a single stimulation program 66 may include a single stimulation set 60, whereas in a more complex case twenty-four stimulation programs 66 may each include eight stimulation sets 60.

In one embodiment, stimulation system 10 executes only a single stimulation program 66 in response to user selection of that stimulation program for execution. In another embodiment, during a stimulation period, stimulation system 10 executes a sequence of pre-programmed stimulation programs 66 for each stimulation lead 14 until the stimulation period ends. Depending on the length of the stimulation period and the time required to execute a sequence of stimulation programs 66, the sequence may be executed one or more times. For example, the stimulation period may be defined in terms of a predetermined number of cycles each involving a single execution of the sequence of stimulation programs 66, the sequence of stimulation programs 66 being executed until the predetermined number of cycles has been completed. As another example, the stimulation period may be defined in terms of time, the sequence of stimulation programs 66 being executed until a predetermined time interval has elapsed or the patient or another user manually ends the stimulation period. Although a sequence of stimulation programs 66 is described, a single stimulation program being executed one or more times during a stimulation period according to particular needs. Furthermore, the present invention contemplates each stimulation program 66 being executed substantially immediately after execution of a previous stimulation program 66 or after a suitable time interval has elapsed since the completion of the previous stimulation program 66.

Where stimulation system 10 includes multiple stimulation leads 14, stimulation programs 66 for one stimulation lead 14 may be executed substantially simultaneously as stimulation programs 66 for one or more other stimulation leads 14, may be alternated with stimulation programs 66 for one or more other stimulation leads 14, or may be arranged in any other suitable manner with respect to stimulation programs 66 for one or more other stimulation leads 14.

In general, each stimulation program 66 may, but need not necessarily, be set up for electrical stimulation of different target nerve tissue. As an example, for electrical stimulation of the spinal cord, one or more stimulation programs 66 may be set up for therapeutic electrical stimulation of certain target nerve tissue in the spinal cord and one or more other stimulation programs 66 may be set up for electrical stimulation certain other target nerve tissue in the spinal cord.

The present invention contemplates any suitable circuitry within stimulation source 12 for generating and transmitting electrical stimulation pulses for electrical stimulation of target nerve tissue to provide therapeutic paresthesia in an affected region of a person's body. Example circuitry that may be suitable for use is illustrated and described in U.S. Pat. No. 6,609,031 B1, which is hereby incorporated by reference herein as if fully illustrated and described herein.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method for maintaining a constant level of paresthesia in a person's body, comprising:
   generating stimulation pulses using a stimulation source;
   transmitting the stimulation pulses from the stimulation source to one or more stimulation electrodes implanted proximate target nerve tissue in a nerve pathway in the person's body to cause the stimulation electrodes to deliver the stimulation pluses to the target nerve tissue to cause paresthesia in a portion of the person's body corresponding to the target nerve tissue, each stimulation pulse inducing an action potential in each of a plurality of stimulated nerve fibers within the nerve pathway;
   for each stimulation pulse, detecting a compound action potential associated with that stimulation pulse using one or more sensing electrodes implanted proximate the nerve pathway at some distance caudal along the nerve pathway from the one or more stimulation electrodes, the compound action potential comprising the action potentials of the plurality of nerve fibers within the nerve pathway that are stimulated by that stimulation pulse;
   transmitting one or more signals reflecting the one or more detected compound action potentials associated with one or more stimulation pulses; and
   modifying one or more stimulation parameters of the stimulation pulses generated by the stimulation source and delivered to the target nerve tissue by the one or more stimulation electrodes, based on the one or more signals reflecting the detected compound action potentials associated with one or more stimulation pulses, to maintain a substantially constant level of paresthesia in the portion of the person's body corresponding to the target nerve tissue.

2. The method of claim 1, wherein modifying one or more stimulation parameters of the stimulation pulses comprises:
   increasing at least one of the amplitude and the pulse width of the stimulation pulses generated by the stimulation source if the one or more signals reflecting the one or more detected compound action potentials indicate that the one or more detected compound action potentials are below a first specified threshold to maintain a substantially constant level of paresthesia in the portion of the person's body corresponding to the target nerve tissue; and
   decreasing at least one of the amplitude and the pulse width of the stimulation pulses generated by the stimulation source if the one or more signals reflecting the one or more detected compound action potentials indicate that the one or more detected compound action potentials are above a second specified threshold to maintain a substantially constant level of paresthesia in the portion of the person's body corresponding to the target nerve tissue.

3. The method of claim 2, wherein at least one of the first and second specified thresholds is pre-programmed.

4. The method of claim 3, wherein at least one of the first and second specified thresholds is user-specified and the method further comprises allowing the user to adjust the at least one user-specified threshold during operation of the method.

5. The method of claim 2, wherein the first and second specified thresholds have different amplitudes to help avoid hysteresis.

6. The method of claim 1, wherein:
   the nerve pathway comprises the person's spinal cord; and
   the stimulation lead and the sensing device are adapted for implantation into the epidural space proximate the person's spinal cord.

7. The method of claim 1, wherein the nerve pathway is associated with at least one of:
   a peripheral nerve;
   a root nerve;
   a cranial nerve; and
   the brainstem.

8. The method of claim 1, wherein the compound action potential associated with each stimulation pulse comprises the sum of the action potentials in 10 the plurality of nerve fibers stimulated by that stimulation pulse.

9. The method of claim 1, wherein the sensing electrodes are located at a sufficient distance from the stimulation electrodes along the nerve pathway such that a stimulus artifact associated with each stimulation pulse has occurred when the compound action potential associated with that stimulation pulse is detected by the sensing electrodes.

10. The method of claim 1, wherein:
   the sensing electrodes are physically integrated with the stimulation electrodes on a stimulation lead.

11. The method of claim 1, wherein the sensing electrodes comprise a sensing lead that is physically distinct from the stimulation electrodes.

* * * * *